US00RE35653E

United States Patent [19]

Aebischer et al.

[11] E Patent Number: Re. 35,653

[45] Reissued Date of Patent: Nov. 4, 1997

[54] IN VIVO DELIVERY OF NEUROTRANSMITTERS BY IMPLANTED, ENCAPSULATED CELLS

[75] Inventors: Patrick Aebischer; Shelley R. Winn; Pierre M. Galletti, all of Providence, R.I.

[73] Assignee: Brown University Research Foundation, Providence, R.I.

[21] Appl. No.: 85,504

[22] Filed: Jun. 30, 1993

Related U.S. Patent Documents

Reissue of:

[64] Patent No.: 4,892,538
Issued: Jan. 9, 1990
Appl. No.: 121,626
Filed: Nov. 17, 1987

[51] Int. Cl.[6] ..... A61K 9/22

[52] U.S. Cl. ..... 604/891.1; 128/898; 128/899; 424/424

[58] Field of Search ..... 604/890.1, 891.1, 604/27, 28, 36, 43, 93, 116; 623/11, 12; 424/422–424; 128/897–899

[56] References Cited

U.S. PATENT DOCUMENTS

| | | | |
|---|---|---|---|
| 3,093,831 | 6/1963 | Jordan | 623/12 |
| 4,241,187 | 12/1980 | White | 435/284 |
| 4,352,883 | 10/1982 | Lim | 623/11 |
| 4,353,888 | 10/1982 | Sefton | 623/11 |
| 4,378,016 | 3/1983 | Loeb | 128/260 |
| 4,391,909 | 7/1983 | Lim | 623/11 |
| 4,402,694 | 9/1983 | Ash et al. | 604/891 |
| 4,686,098 | 8/1987 | Kopchick et al. | 623/11 |

FOREIGN PATENT DOCUMENTS

| | | |
|---|---|---|
| 0147939 | 7/1985 | European Pat. Off. . |
| 0161640 | 11/1985 | European Pat. Off. . |
| 0213908 | 11/1987 | European Pat. Off. . |
| WO 87/03802 | 7/1987 | WIPO . |

OTHER PUBLICATIONS

Bjorklund et al, "Cross–Species Neural Grafting in a Rat Model of Parkinsons' Disease," Nature, vol. 298, pp. 652–654, Aug. 12, 1982.

Sun et al, Diabetes, vol. 26, No. 12, pp. 1136–1139, Dec. 1977.

Annals of the N.Y. Academy of Sciences, "Hope for a New Neurology" pp. 105–126, vol. 257, Dec. 31, 1985.

Annals of the N.Y. Academy of Sciences, "Cell and Tissue Transplantation into the Adult Brain", vol. 495, pp. 306–333, 473–496, 581–597, 598–605, 606–622, 786–791, 804–806, Jun. 30, 1987.

Brundin et al, Exp. Brain Res. (1985) 60:204–208.

Calne et al, The Lancet (1969), Nov. 8, 1969, pp. 973–976.

Calne et al. Bri. Med. J. (1974), 4:442–444.

Dichter, "The Epilepsies and Convulsive Disorders," in *Principles of Internal Medicine* (Harrison et al, eds.) 10th Ed., 1983, pp. 2125–2127.

Freed et al, Nature (1981) 292:351–352.

Hefti et al, Brain Res. (1985) 348:283–288.

Perlow et al, Science (1979) 204:643–647.

Stenaas and Stenaas, Acta. Neuropath. (Berl.) (1978) 41:145–155.

*Primary Examiner*—Vanitha Alexander
*Attorney, Agent, or Firm*—Fish & Neave; Ivor R. Elrifi; Petrina S. Hsi

[57] ABSTRACT

Methods and devices are disclosed for the delivery of a neurotransmitter from an implanted, neurotransmitter-secreting cell culture to a target region in a subject. The cell culture is maintained within a biocompatible, semipermeable membrane which permits the diffusion of the neurotransmitter therethrough while excluding viruses, antibodies, and other detrimental agents present in the external environment from gaining access. Implantable cell culture devices are disclosed, some of which may be retrieved from the subject, replaced or recharged with new, neurotransmitter-secreting cell cultures, and reimplanted.

24 Claims, 1 Drawing Sheet

IN VIVO DELIVERY OF NEUROTRANSMITTERS BY IMPLANTED, ENCAPSULATED CELLS

Matter enclosed in heavy brackets [ ] appears in the original patent but forms no part of this reissue specification; matter printed in italics indicates the additions made by reissue.

BACKGROUND OF THE INVENTION

The technical field of this invention is the treatment of neurological diseases and, in particular, the treatment of neurotransmitter-deficiency diseases.

Neurotransmitters are small molecules (less than 1000 daltons molecular weight) which act as chemical means of communication between neurons. They are synthesized by the presynaptic neuron and released into the synaptic space where they are then taken up by postsynaptic neurons.

Neurotransmitter deficits have been implicated in various neurological diseases. Lack of neurotransmitter-mediated synaptic contact causes neuropathological symptoms, and can also lead to the ultimate destruction of the neurons involved. However, it has been discovered that localized delivery of the relevant neurotransmitter to the target tissue may reverse the symptoms without the need for specific synatic contact.

For example, paralysis agitans, more commonly known as Parkinson's disease, is characterized by a lack of the neurotransmitter, dopamine within the striatum of the brain, secondary to the destruction of the dopamine secreting cells of the substantia nigra. Affected subjects demonstrate a stooped posture, stiffness and slowness of movement, and rhythmic tremor of limbs, with dimentia being often encountered in very advanced stages of the disease. These clinical symptoms can be improved by the systemic administration of dopamine precursors, such as levodopa (L-dopa)(Calne et al., (1969) Lancet ii:973–976) which are able to cross the blood-brain barrier, and to be converted into dopamine in the brain, or agonists, such as bromocriptine (Calne et al., (1974) Bri. Med. J. 4:442–444). Dopamine, itself, cannot be administered systemically because of its inability to cross the blood-brain barrier.

However, one of the drawbacks of this type of chemical therapy is that other neurological structures using dopamine as a neurotransmitter are affected. In addition, it becomes difficult to administer the correct drug dosage with time because the "therapeutic window" narrows (i.e., just after administration, the patient is overdosed, exhibiting excessive spontaneous movement; some time therafter the drug level may become insufficient, causing the patient to again express parkinsonian symptoms). Therefore, what is needed is a method of continuous or constitutive delivery of a required neurotransmitter to a localized target region which is deficient in that neurotransmitter.

Recently, remedial transplantation of neurotransmitter-secreting tissue has been accomplished using the patient's own tissue so as not to elicit an immune response. For example, dopamine-secreting tissue from the adrenal medulla of Patients suffering from Parkinson's disease has been implanted in their striatum with reasonable success. However, this procedure is only used in patients less than 60 years of age, as the adrenal gland of older patients may not contain sufficient dopamine-secreting cells. This restriction limits the usefulness of this procedure as a remedy since the disease often affects older people.

Furthermore, brain surgery involves a substantial risk of morbidity, and abdominal surgery performed to excise portions of the adrenal gland Poses substantial risks as well. Moreover, it is not actually known whether it is the implanted cells actually producing dopamine, or the trauma of the surgery, itself, which alleviates the clinical symptoms. In fact, stereotaxic surgery, or the placement of precisely localized lesions in the brain has been practiced in younger, less affected patients to relieve parkinsonian symptoms. The procedure is risky, however, and opinions among neurosurgeons still differ as to the best way of making the lesion and what its ideal location should be.

Alternatives have been the transplantation of either allograft (identical tissue from another of the same species), or xenograft (similar tissue from another of a different species) dopamine-secreting tissue. However, recent studies have shown that although the brain is considered "immunopriviledged", rejection ultimately occurs with both allo- and xenografts. This problem necessitates the co-adminstration of immunosuppressors, the use of which renders their own set of complications and deleterious side-effects.

Therefore, there exists a need for improved therapies for neurotransmitter-deficiency diseases in general, and in particular, a need for systems which can augment or replace the functions of dysfunctional neurotransmitter-producing areas of the brain without causing excessive trauma. More specifically, there exists a need for a method of providing a neurotransmitter to a localized region of the nervous system of a subject deficient in this hormone, the correct dosage of which will be continually or constitutively delivered over time.

Accordingly, it is an object of the present invention to provide a method for delivering a neurotransmitter to a subject deficient in that neurotransmitter, and to provide a method of delivering a neurotransmitter to a localized target region of the nervous system of a subject. It is another object of the present invention to provide a method of delivering a neurotransmitter to a subject in a constitutive manner, and to provide an implantable device which is capable of constitutively delivering a neurotransmitter to a localized region of the nervous system of a subject deficient in that neurotransmitter.

Yet another object is to provide an implantable cell culture device which is retrievable, and whose contents are renewable with new and/or additional neurotransmitter-secreting cells.

A further object is to provide a cell culture device which protects the cells therein from an immunological response or from vital infection, while allowing the delivery of a neurotransmitter therefrom.

SUMMARY OF THE INVENTION

Methods and devices are disclosed herein for the constitutive delivery of a neurotransmitter from a culture of neurotransmitter-secreting cells to a subject suffering from a neurological deficiency. It has been discovered that selectively permeable membranes have the ability to protect transplanted neurotransmitter-secreting cells from autoimmune and viral assault, while allowing essential nutrients, cellular waste products, and secreted neurotransmitter to diffuse therethrough. In accordance with the method of present invention, at least one neurotransmitter-secreting cell is encapsulated within such a membrane and implanted into a subject, where it is maintained protectively while supplying neurotransmitter to the local internal environment of that subject.

The terms "selectively permeable" and "semipermeable" are used herein to describe biocompatible membranes which allow the diffusion therethrough of solutes having a molecular weight of up to about 50,000 daltons. The preferred semipermeable membrane materials include polymeric materials selected from the group consisting of acrylic copolymers, polyvinylidene fluoride, polyurethane isocyanates, polyalginate, cellulose acetate, polysulfone, polyvinyl alcohols, polyacrylonitrile, derivatives, and/or mixtures thereof.

In one aspect of the invention encapsulated, neurotransmitter-secreting cells may be implanted within a subject and then retrieved when they have expired, are no longer functional, or are no longer required to correct the neurological disorder. Retrieval can be accomplished by means of a biocompatible, nonresorpable guide wire which is attached to the encapsulating membrane.

In another aspect of the present invention, the encapsulating membrane is in the shape of a tube, with its openings being covered by removable plugs or caps. Such a construct enables the easy replacement of cells within the membrane with other cells through the uncovered tube openings after retrieval from the subject via the attached guide wire.

The encapsulated cells of the present invention may be allografts, or cells obtained from matched tissue of another of the same species. Alternatively, the cells may be xenografts, or cells obtained from a similar tissue of a different species. However, regardless of their source, the cells to be transplanted may be any cells which synthesize and secrete a particular neurotransmitter which is deficient in the nervous system of a subject.

One preferred neurotransmitter is dopamine which is secreted by cells of the adrenal medulla, embryonic ventral mesencephalic tissue, and the neuroblastic cell lines. Other neurotransmitters include gamma aminobutyric acid (GABA), serotonin, acetylcholine, noradrenaline, and other compounds necessary for normal nerve functions. Various cell lines are also known or can be isolated which secrete these neurotransmitters. Cells from such cell lines can likewise be encapsulated according to the present invention. The encapsulated cells can also synthesize and secrete an agonist, analog, derivative, or fragment of a neurotransmitter which is active including, for example, cells which secrete bromocriptine, a dopamine agonist, and cells which secrete L-dopa, a dopamine precursor.

The region targeted for implantation of the neurotransmitter-secreting cells is preferably the brain of the subject since this is often the site of many neurological deficiencies or disorders.

The invention will next be described in connection with certain illustrated embodiments. However, it should be clear that various modifications, additions, and subtractions can be made without departing from the spirit or scope of the invention. The present invention should not be read to require, or be limited to, particular cell lines described by way of sample or illustration.

BRIEF DESCRIPTION OF THE DRAWINGS

The invention itself can be more fully understood from the following description when read together with the accompanying drawings.

DETAILED DESCRIPTION OF THE INVENTION

Figure 1:
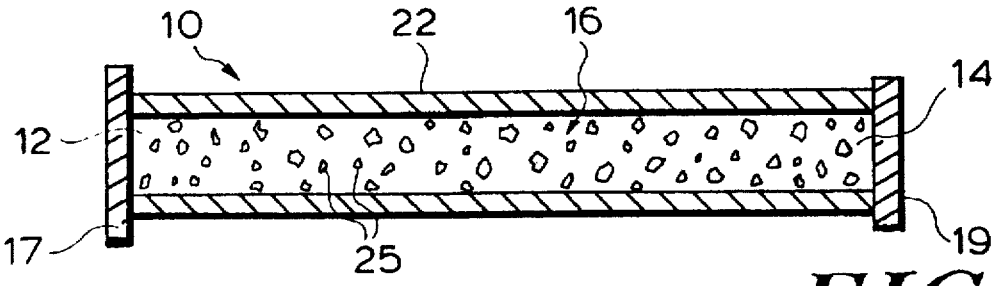
FIG. 1 is a schematic illustration of an implantable cell culture device for delivering a neurotransmitter, according to one aspect of the present invention.

A method for the constitutive delivery of neurotransmitter to a localized target region of a subject suffering from a neurological deficiency, and a device for practicing this method has been devised. The method includes encapsulating neurotransmitter-secreting cells within a protective, selectively permeable membrane or cell culture device, and implanting the device in a target region of a subject. The target region may be any part of the subject's anatomy which responds to and requires neurotransmitter for normal function. This region may be any part of the nervous system, but will most often be the brain, as it is the source of numerous neurological dysfunctions.

The cells to be encapsulated and implanted may be any which secrete the desired neurotransmitter. They may be allografts, or cells from another of the same species as the subject in which they are to be implanted, or they may be xenografts, or those from another of a different species. More particularly, they may be a component of a body organ which normally secretes a particular neurotransmitter in vivo. Preferable cells include those dopamine-secreting cells from the embryonic ventral mesencePhalon, from neuroblastoid cell lines or from the adrenal medulla.

More generally, any cell which secretes a neurotransmitter or a precursor, analog, derivative, agonist or fragment of a desired neurotransmitter having similar neurotransmitter activity can be used, including, for example, cells which elicit L-dopa, a precursor of dopamine and bromocriptine, a dopamine agonist.

Further, any cells which have been genetically engineered to express a neurotransmitter or its agonist, precursor, derivative, analog, or fragment thereof which has similar neurotransmitter activity are also useful in practicing this invention. Thus, in such an approach, the gene which encodes the neurotransmitter, or its analog or precursor is either isolated from a cell line or constructed by DNA manipulation. The gene can then be incorporated into a plasmid, which, in turn, is transfected into a set of cells for suppression. The cells which express the neurotransmitter can be grown in vitro until a suitable density is achieved. A portion of the culture is then used to seed the implantable device. (See, e.g., Maniatis et al., Molecular Cloning (1982), herein incorporated by reference for further discussion of cloning vehicles and gene manipulation procedures.)

Regardless of the source, the neurotransmitter-secreting cells as tissue fragments or culture aggregates are placed into an implantable, selectively permeable membrane which protects them from deleterious encounters with viruses and elements of the immune system. Such protection is particularly important for preserving allografts or xenografts which are eventually considered foreign even in the "immunoprivileged" brain. Therefore, the membrane should bar viruses, macrophages, complement, lymphocytes, and antibodies from entry while allowing the passage of nutrients, gases, metabolic breakdown products, other solutes, and the neurotransmitter to pass therethrough. Accordingly, any biocompatible and nonresorpable materials having pores enabling the diffusion of molecules having a molecular weight of up to about 50,000 daltons are useful for practicing the Present invention, with acrylic copolymers, polyvinylidene fluoride, polyurethane isocyanates polyalginate, cellulose acetate, polysulfone, polyvinyl alcohols, polyacrylonitrile, derivatives, and mixtures thereof being the most preferable.

The cell culture device may take any shape which will accommodate the cells to be encapsulated, and which will not cause undue trauma upon surgical implantation. A preferable implantable cell culture device 10 shown in FIG. 1 is a tubular, selectively permeable membrane 22 having ends 12 and 14 through which neurotransmitter-secreting cells 25 are loaded into cell compartment 16. Ends 12 and 14 may then be permanently occluded with caps 17 and 19 or, alternatively, with an epoxy glue or sutures of a biocompatible and nonresorpable material like polypropylene.

The device 20 as shown in FIG. 1 can be surgically implanted into the brain of a subject such that membrane 22 is in immediate contact with brain tissues.

Figure 2:
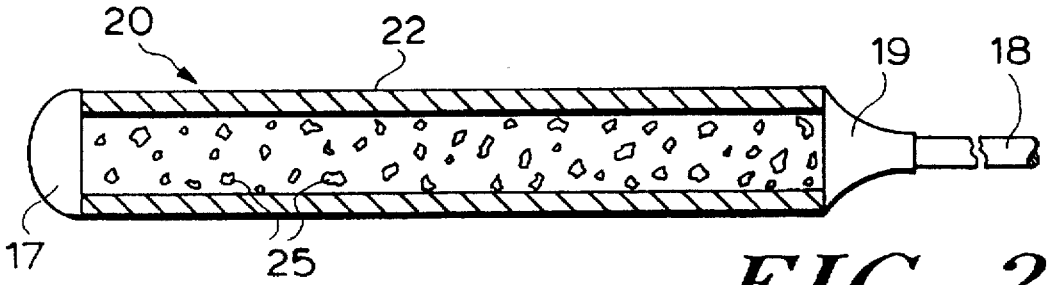
FIG. 2 is a schematic illustration of an implantable and retrievable cell culture device for delivering a neurotransmitter, according to another aspect of the invention.

The method of the present invention may include an additional step whereby the initially encapsulated and implanted cells are removed from the subject in the event that they cease to produce neurotransmitter, expire, or are no longer needed to correct the neurological dysfunction. As illustrated in FIG. 2, retrieval of implanted cell culture device 20 is preferably accomplished by means of guide wire 18 which is permanently attached to end cap 17 or 19. This wire may be constructed of any nonresorpable, biocompatible material with enough tensile strength to support the cell culture device.

Figure 3:
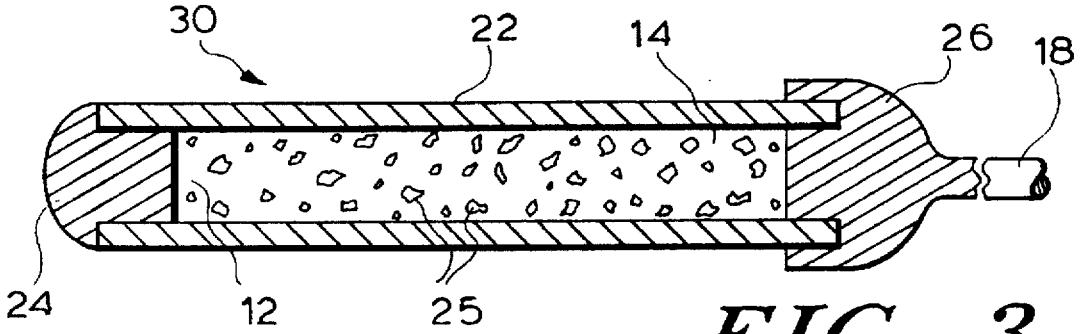
FIG. 3 is a schematic illustration of an implantable, retrievable, and rechargeable cell culture device for delivering a neurotransmitter, according to yet another aspect of the invention.

The cellular contents of the device may be replaced in the event that it is desirable to reimplant the device after its retrieval. A exemplary cell culture device useful in practicing this method is shown in FIG. 3. Device 30 is tubular, having ends 12 and 14 reversibly covered with removable, friction-fitted caps 22 and 24, respectively, to enable the extraction and replacement of cells 25 in cell compartment 16 with new cells.

The device 30 as shown in FIG. 3 can be surgically implanted into the brain of a subject such that guide wire 18 is located directly under the epithelial tissues of the head, and membrane 22 is in immediate contact with brain tissue.

The following examples more fully illustrate preferred features of the invention.

EXAMPLE I

Implantation of Selectively Permeable Membrane Tubes into the Brain

XM-50 tubes (Amicon Corp., Lexington, Mass.) consisting of polyvinyl chloride acrylic copolymer and having an internal diameter (ID) of 600μ and a wall thickness of 100μ were obtained. Each tube was composed of a selectively permeable inner membrane supported by a trabecular network which was covered by an open polymer film. The inner membrane had a nominal molecular weight cut-off of 50,000 daltons. The polymer tubes were cleaned and sterilized, cut into sections approximately 3–4 mm in length, and capped at each end with an epoxy polymer glue.

Young male albino CD-1 rats (250–300 g) were anesthetized with an intraperitoneal injection of sodium thiopental (25 mg/kg), and Placed in a stereotaxic apparatus. The parietal cortex was exposed through a small craniotomy. The polymer tubes were implanted by gently pushing them into the parietal cortex parenchyma. Skin closure was achieved with 6.0 polypropylene sutures. Aseptic surgical technique was maintained through the procedure. Cohorts of 3 animals received 3–4 mm length XM-50 tubes for 1, 2, 4, and 12 weeks.

At retrieval time, deeply anesthetized animas were perfused transcardially with 200 ml of a heparinized Tris buffer solution followed by 200 ml of 4% paraformaldehyde and 0.1% glutaraldehyde in Tris buffer. Samples of the striatum were excised and post-fixed overnight by immersion, and subsequently were transferred into 15% and then 30% buffered sucrose. Once equilibrated, the samples were quick-frozen in dry ice. Thick sections 20–25 mm were cut on a frozen sliding microtome. Sections chosen for immunostaining were then incubated, free-floating, in primary antiserum for 3 days at 4° C. in 0.1% Triton X-100, 0.1M Tris buffer, pH 7.4 with blanking serum. Primary antiserol used were to glial fibrillary acidic protein (GFAP) (a gift from Dr. Larry Eng, Stanford University, Palo Alto, Calif.) and to neuron-specific enolase (NSE) (Dakopatts, Denmark). Section were rinsed briefly in Tris buffer prior to incubation in a secondary swine anti-rabbit antiserum (1:225) in Tris buffer at room temperature. After rinsing, sections were incubated in a soluble complex of rabbit peroxidase-antiperoxidase (PAP) (Dakopatts, Denmark) (1:100), and the reaction visualized with a solution of diaminobenzidine and hydrogen peroxide. Sections were mounted, counterstained with cresyl violet, dehydrated, and coverslipped. Reaction to the hollow tubes was analyzed with a Zeiss IM 35 microscope (Oberkochen, Fed. Rep. West Germany) interfaced with a video monitor.

For ultrastructural examination, anesthetized animals were transcardially perfused with a modified Karnovsky's fixative. Samples were post-fixed in 0.75% osmium tetroxide, dehydrated, an then embedded in Spurr's low viscosity resin. Semi-thin sections for light microscopy were cut and stained with toluidine blue and basic fuchsin. Ultra-thin sections of selected specimens were stained with Reynold's lead citrate and uranyl acetate. Electron microscopic analysis was performed with a Phillips 410.

No neurological deficit was observed in any of the implanted animals. A necrotic zone was not detected around the polymer tubes for any time period as assessed by the Nissl stain. NSE immunolabeling showed the preservation of the typical columnar orientation of the cortical neurons Neurons with typical apical dendrites were observed in close apposition to the polymer capsule membrane. Reactive astrocytes as determined by GFAP immunolabeling were observed up to 400 μm from the polymer capsule during the first 2 weeks post-implantation. The area in which the reactive astrocytes were detected diminished with time such that at 12 weeks, immunoreactive astrocytes were seen only in close apposition to the polymer membrane material.

Transmission electron microscopy (TEM) showed minimal collagen deposition around the polymer capsule. Normal synapses were seen within 3–5μ of the brain-implant interface. Foreign body giant cells were not detected surrounding the polymer tube. Microglia identified by their bipolar appearance and rod-like nucleus were observed in the wall trabeculae of the tubes. No cells entered the internal tubular space, demonstrating the selectively permeable nature of the polymer membrane.

EXAMPLE II

Implantation of Encapsulated Ventral Mesencephalon in the Brain

Embryonic (E14–16) mouse ventral mesencephalon were dissected into 1 $mm^3$ pieces, put in RPMI 1640 (Gibco Laboratory, Grand Island, N.Y.) and then cut into 8–10 smaller pieces. These pieces were mechanically placed into the polymer tube. The tube ends were then capped with an epoxy polymer glue. Loaded capsules were implanted in the parietal brain cortex of rats as described above. Implants were allowed to remain for 1, 2, 4 and 8 weeks before retrieval. Animals with implants were sacrificed and examined as described in EXAMPLE I above.

Mouse embryonic mesencephalic tissue retrieved from polymer tubes implanted in the rat brain consisted of intact tissue interspersed with some necrotic tissue at the various implantation times. The tissue was usually centrally located in the tube. TEM demonstrated the presence of well preserved neuronal cell bodies, axons, synapses, and glial cells.

The presence of intact cells in the polymer capsule after several weeks of implantation suggests that free diffusion of nutrients occurs through the permselective membrane, and that the tissue is immunoprotected by the polymer membrane. The minimal tissue reaction to the polymer material by the host brain constitutes a favorable factor for free diffusion through the polymer membrane

EXAMPLE III

Implantation of Encapsulated Dopamine-secreting Cells into Rats with Induced Parkinsonism Experimental parkinsonism can be induced in rats by unilateral destruction of the mesostriatal dopamine system using the neurotoxin 6-hydroxydopamine (6-OHDA). The drug-induced unilateral lesions initiate a rotational or circling response that can be easily quantitated by pharmacological methods. Under the influence of the dopamine agonist metamphetamine, rotational behavior, i.e., the number of rotations per time interval correlates to the extent of the lesion. Metamphetamine induces the animal to rotate ipsilaterally (i.e., towards the side of the lesion).

Lesions were induced with 12 μg 6-OHDA-HCl disolved in 8μl 0.2 mg ascorbic acid/ml 0.9% NaCl. This solution was injected stereotaxically over a 5 minute period.

The animals were tested for unilateral lesions 7–10 days after injection. 5 mg metamphetamine per kg rat was injected. Rotational behavior was then recorded 30 minutes after injection. Rotations were recorded over 6 one min. intervals with at least a 2 min. rest period between recordings. To stimulate the animals a high frequency ultrasonic device was used during the one minute recording intervals. Animals that rotate consistently at least 8 turns/min. were used for the transplantation test.

Embryonic (E14–16) mouse mesencephalic tissue was isolated, placed in tissue culture medium, and cut into tiny pieces. These tissue fragments, or alternatively cells from the LA-N-5 human neuroblastoma cell line (a gift of J. de Ybenes, Columbia Univ., N.Y.) were aspirated or mechanically inserted into the lumen of 3–4 mm long polymer capsules which were then capped with a polymer glue.

5 young male albino CD-1 Sprague-Dawley rats (250–300 g) (Charles River Labs) having base-line rotational values in the range of 11–12 turns/min. pretransplantation received mesencephalic xenografts. The filled capsules each containing approximately $10^6$ cells per capsule were transplanted, one capsule per animal, in the caudate/putamen portion of the brain with the hope that part of the capsule would be bathed in the ventricular system.

No significant changes in behavior were observed within the first 2 weeks post-transplantation. By 3 weeks a reduction in rotational behavior became evident. After 4–5 weeks, the animals were rotating about 2–3 turns/min.

We claim:

1. A method of delivering a neurotransmitter to a subject afflicted with a neurotransmitter deficiency comprising the steps of:

encapsulating at least one neurotransmitter-secreting cell within a semipermeable membrane, said membrane allowing the diffusion of the neurotransmitter therethrough while excluding viruses, antibodies and other detrimental agents present in the external environment; and implanting said encapsulated cell into a target region within a subject's brain, such that the encapsulated cell secretes the neurotransmitter and thereby provide constitutive delivery of the neurotransmitter to the target region to treat the deficiency.

2. The method of claim 1 wherein said encapsulating step further comprises disposing said neurotransmitter-secreting cell within said semipermeable membrane, said membrane allowing the diffusion of solutes having a molecular weight of up to about 50,000 daltons therethrough.

3. The method of claim 1 wherein said encapsulating step further comprises disposing said neurotransmitter-secreting cell within, said semipermeable membrane, said membrane being composed of a material selected from the group consisting of acrylic copolymers, polyvinylidene fluoride, polyurethane isocyanates, polyalginate, cellulose acetate, polysulfone, polyvinyl alcohols, polyacrylonitrile, and derivatives and mixtures thereof.

4. The method of claim 1 wherein said implanting step is reversible, said semipermeable membrane being attached to a retrievable, nonresorpable, and biocompatible guide wire which enables removal of said device from said subject.

5. The method of claim 4 wherein said encapsulating step further comprises disposing said neurotransmitter-secreting cell within said membrane in a retrievable fashion, said membrane having a tubular shape with a first end and a second end, said ends each having a cap element removably attached thereto to enable extraction of said cells therein.

6. The method of claim 1 wherein said encapsulating step further comprises disposing within said membrane a neurotransmitter-secreting cell, said neurotransmitter being dopamine, and said neurotransmitter-secreting cell being selected from the group consisting of adrenal medulla tissue, ventral mesencephalic embryonic tissue, and neuroblastoid tissue.

7. The method of claim 1 wherein said encapsulating step further comprises disposing within said membrane a cell which secretes one of the group consisting of a precursor, analog, agonist, derivative, and fragment of a neurotransmitter which has neurotransmitter activity.

8. The method of claim 7 wherein said neurotransmitter is dopamine, and said precursor is L-dopa.

9. The method of claim 7 wherein said neurotransmitter is dopamine, and said analog is bromocriptine.

10. The method of claim 1 wherein said encapsulating step further comprises disposing within said membrane a neurotransmitter-secreting cell, said cell being a tissue allograft.

11. The method of claim 1 wherein said encapsulating step further comprises disposing within said membrane a neurotransmitter-secreting cell, said cell being a tissue xenograft.

12. The method of claim 1 wherein said implanting step further comprises implanting said encapsulated, neurotransmitter-secreting cell in said target region of said subject, said target region being the brain.

13. A cell culture device for implantation within a subject for the constitutive delivery of a neurotransmitter to a target area of said subject, said device comprising:

a semipermeable membrane permitting the diffusion of the neurotransmitter therethrough, while excluding viruses, antibodies, and other detrimental agents present in the external environment; and at least one neurotransmitter-secreting cell disposed within the membrane, said cell being capable of secreting neurotransmitter without direct neuronal contact with said target area.

14. The device of claim [14] *13* wherein said semipermeable membrane is permeable to solutes having a molecular weight of up to about 50,000 daltons.

15. The device of claim [14] *13* wherein said semipermeable membrane comprises a material selected from the group consisting of acrylic copolymers, polyvinylidene fluoride, polyurethane isocyanates, polyalginate, cellulose acetate, polysulfone, polyvinyl alcohols, polyacrylonitrile, and derivatives and mixtures thereof.

16. The device of claim [14] *13* wherein said neurotransmitter-producing cell further comprises a tissue allograft.

17. The device of claim [14] *13* wherein said neurotransmitter-producing cell further comprises a tissue xenograft.

18. The device of claim [14] *13* wherein said neurotransmitter is dopamine, and said neurotransmitter-secreting cell is selected from the group consisting of adrenal medulla tissue, ventral mesencephalic embryonic tissue, and neuroblastoid tissue.

19. The device of claim [14] *13* wherein said neurotransmitter is selected from the group consisting of agonists, precursors, analogs, derivatives, and fragments of a neurotransmitter which have neurotransmitter activity.

20. The device of claim 19 wherein said neurotransmitter precursor is L-dopa.

21. The device of claim 19 wherein said neurotransmitter analog is bromocriptine.

22. The device of claim [14] *13* further comprising a retrievable, nonresorpable, and biocompatible guide wire attached to said semipermeable membrane, so as to enable the removal of said device from said subject.

23. The device of claim [14] *13* wherein said semipermeable membrane is tubular, having at least one end with a cap element reversibly attached thereto.

24. The device of claim 22 wherein said neurotransmitter-secreting cell is disposed within said semipermeable membrane in a removable fashion, said membrane being tubular, having at least one end with a cap element reversibly attached thereto, so as to enable extraction of said cells therein.

* * * * *